United States Patent [19]

Corey

[11] Patent Number: 4,955,866

[45] Date of Patent: Sep. 11, 1990

[54] HYPODERMIC NEEDLE RECAPPING DEVICE

[75] Inventor: George A. Corey, Duluth, Minn.

[73] Assignee: University of Florida, Gainesville, Fla.

[21] Appl. No.: 352,198

[22] Filed: May 16, 1989

Related U.S. Application Data

[63] Continuation-in-part of Ser. No. 259,894, Oct. 19, 1988, abandoned.

[51] Int. Cl.$^5$ .............................................. A61M 5/32
[52] U.S. Cl. .................................. 604/192; 604/198; 604/263
[58] Field of Search ............... 604/198, 263, 187, 192, 604/110

[56] References Cited

U.S. PATENT DOCUMENTS

| | | | |
|---|---|---|---|
| 4,778,453 | 10/1988 | Lopez | 604/198 |
| 4,790,828 | 12/1988 | Dombrowski et al. | 604/198 |
| 4,804,371 | 2/1989 | Vaillancourt | 604/198 |

*Primary Examiner*—John D. Yasko
*Attorney, Agent, or Firm*—Dennis P. Clarke

[57] ABSTRACT

A recapping device is provided for use with medical devices including all hollow and solid medical needles of the type used for entry into the body and into closed intravenous and intraarterial systems for access, sampling, and injection of medications, and are withdrawn after use. The recapping device includes a hollow sleeve encircling a portion of the needle and having a distal end aperture adapted to permit the sleeve to slide between a first position on the medical device wherein the needle is exposed to enable use of the needle, and a second position characterized by the distal end of the needle being contained within the distal end capped hollow sleeve, and the device may optionally contain a housing for a free-floating fenestrated disk, which, upon movement of the device to its second position wherein the tip of the needle exits the distal end aperture, shifts position to provide an obstruction at that aperture. A securing means for the hollow sleeve, such as a tether, is provided for permitting substantially free slidable movement of the hollow sleeve between the first and second positions.

29 Claims, 5 Drawing Sheets

HYPODERMIC NEEDLE RECAPPING DEVICE

CROSS REFERENCES TO RELATED APPLICATIONS

This application is a continuation-in-part of U.S. patent application Ser. No. 259,894, filed Oct. 19, 1988 now abandoned.

BACKGROUND OF THE INVENTION

1. Field of the Invention

The present invention relates to a safety shield for hollow and solid medical needles, of the type which are used for entry into the body, into closed intravenous and intraarterial catheter systems for access, sampling, injection of medications, and transferring specimens to closed containers, and are withdrawn after use, the safety shield performing a self-recapping function for the sharp tip of the needle.

2. Description of the Prior Art

Devices of known construction which utilize hollow medical needles include syringes with built-in needles, syringes with removable needles, vacuum-tube phlebotomy sets with removable needles, devices for catheter-over-needle cannulation of veins or arteries, devices for needle-over-catheter cannulation of veins or arteries, and trocar (solid needle)-and-catheter devices. Such devices are used for entering body cavities or spaces, the circulatory system, closed intravenous and intraarterial catheter systems, or specimen containers. All of these devices have in common the features of having a sharp end which can easily penetrate human skin, and having the ability to retain pathogens when withdrawn from a human body or closed catheter system which communicates with a human body, thus endangering the user of the device, in that accidental injury and self-contamination by the sharp point after use are possible.

Such known devices are supplied to the user with some form of cap that covers the sharp point prior to use. The protective caps known in the art provide little provision for safely replacing the cap on the needle point. After the needle and associated devices known in the art have been used, the needle and device must be placed in a puncture resistant container to be discarded. Injury and self-contamination due to accidential needle sticks may occur, either in the process of attempting to replace the protective cap, or by the lack of such protection on the sharp point in transit to the disposal container [Jagger J., Hunt E.H., Brand-Elnaggar J., Pearson R.D. Rates of needle-stick injury caused by various devices in a university hospital. New Engl J. Med 1988; 319:284-8.].

Accidental needlestick injuries continue to represent a significant percentage of the injuries which occur in the medical field. Appreciation of the extent of the needlestick injury problem was evident when on Aug. 21, 1987, the CDC recommended universal precautions to prevent transmission of HIV in the health-care setting, intended to apply to the care of all patients, not just those known to be infected with HIV or other blood-borne pathogens. [Recommendations or prevention of HIV transmission in health-care settings. MMWR 1987; 36:3S-18S.].

Recommendations pertaining to needlestick injury rely on refraining from recapping, purposely bending or breaking needles by hand, or removing needles from disposable syringes. An example of a specific recommendation is that, after they are used, disposable needles should be placed in puncture-resistant containers (such as product code SN6132, Becton Dickenson & Company, Rutherford, N.J. 07070) located as closed as practicable to the use area. This specific recommendation has been in place since 1982 [Acquired immunodeficiency syndrome (AIDS) precautions for clinical and laboratory staffs. MMWR 1982;31:577-80.].

While currently an unsafe practice, recapping a needle promptly once it is removed from the skin is laudable in intent. A needle on a syringe presents a hazard from the time it leaves the patient's skin until it is placed in a plastic container. During that time it must traverse an unpredictable environment filled with medical personnel, who may be reacting rapidly to extreme emergency, or inattentively to a routine task. Authors reporting a recent study of 326 needlestick injuries have indicated that, as a result of the study, it has yet to be determined whether recapping poses a greater risk than not recapping when a competing hazard is present. [Jagger J., Hunt E.H., Brand-Elnaggar J., Person R.D.; Rates of needle-stick injury caused by various devices in a university hospital. New Engl J Med 1988; 319:284—8.]. Laboratory phlebotomists currently lessen this problem by carrying a small needle container on their phlebotomy tray like that disclosed in U.S. Pat. No. 4,375,859, and marketed under product code 8900 by Sage Products, Cary, Ill. 60013, which allows relatively prompt removal of the used unrecapped needle from the hub of a vacuum-tube phlebotomy set, without proximity between needle point and fingers. This device still requires some unprotected needle transit, is not applicable for use with a variety of needles and related devices used by nursing personnel and physicians.

The Cooperative Needlestick Surveillance Group of the CDC found that of 938 health care workers exposed to potentially infective body fluid, 637 (68%) involved needlestick, and only 280 (44%) of these were preventable by observing recommended precautions [McCray E.; The Cooperative Needlestick Surveillance Group—Occupational risk of the acquired immunodeficiency syndrome among health care workers. N Engl J Med 1986; 314:1127-32.]. These figures suggest that the CDC recommendations would not have been sufficient to avoid 56% of injuries. A 1985 study from a medical center with a large AIDS population found that 15% of 239 housestaff and 10% of 39 laboratory staff had at least one needlestick exposure (voluntary enrollment in that study was 54% and 22% for housestaff and laboratory staff, respectively) [Weiss SH, Saxinger WC, Rechtman D, et al HTLV-III infection among health care workers. JAMA; 254:2089-93.]. This suggests not only an alarming rate of accidental exposure, but a need for improved protection against accidental needlesticks not heretofore believed available.

The CDC guidelines can not minimize the risk of needlestick injury occurring if the phlebotomist enters his/her own skin immediately after removing the needle or after the patient suddenly jerks his/her arm resulting in needle withdrawal. Similar risk occurs when withdrawing a needle from a resistant substance such as the rubber stopper of a vacuum tube, wherein the needle may disengage suddenly from the stopper, and in a reflexive rebound motion, may return to injure the hand holding the vacuum tube [Jagger J, Hunt EH, Brand-Elnaggar J, Pearson RD. Rates of needle-stick injury caused by various devices in a university hospital. New Engl J Med 1988; 319:284—8.]. While an institution can stress the CDC guidelines to its staff, it can not prevent human error or accident.

Several recent U.S. patents have been issued for devices which claim to render more safe the act of recapping a needle. Examples of such devices are found in U.S. Pat. Nos. 4,747,835; 4,659,330; 4,735,617; 4,726,446; 4,629,453; 4,743,233; and 4,747,837. These all require an intentional act on the part of the user to recap the needle, and are therefore not "self-recapping" in any manner of use. Such devices can not generally prevent rebound or similar injuries which occur rapidly after tip withdrawal. U.S. Pat. Nos. 4,747,835; 4,659,330; 4,743,233; and 4,747,837 relate specifically to the hypodermic syringe, require modification thereof, and are thus not applicable to other medical devices other than hypodermic syringes utilizing needles or to unmodified hypodermic syringes. U.S. Pat. Nos. 4,747,835; 4,659,330; 4,726,446; and 4,629,453 require the user to direct the needle point into a cap held in the opposite hand, claiming protection by means of a flange or a handle. While protection may be improved over previously known caps, the devices still require the second hand to be brought into close proximity of the needle point, and therefore the safety of this approach remains questionable.

There exists, therefore, a need in the art for a device which will immediately cap the needle with a penetration-resistant cover as soon as it is withdrawn from the skin to effectively prevent needlestick injuries. Such a device, if effective and sufficiently inexpensive, would likely be used to the exclusion of older venipuncture and needle equipment. Physical, psychological, and financial morbidity following needlestick accidents could be thereby avoided.

It is an object of the present invention to provide such a recapping device which immediately shields a medical needle after withdrawal of the contaminated sharp tip from a patient or other object, thereby significantly reducing the probability of needlestick injuries during disposal or further handling thereof.

It is a further object of the present invention to provide such a recapping device which may effectively close off an aperture in the recapping device through which the medical needle had previously protruded.

SUMMARY OF THE INVENTION

These and other objects are realized by the present invention which provides a medical needle recapping device for use with syringes having built-in needles, syringes having removable needles, vacuum-tube phlebotomy sets with removable needles, devices for catheter-over-needle cannulation of veins or arteries, devices for needle-over-catheter cannulation of veins or arteries, and catheter-and-trocar devices for entering body cavities or the circulatory system. Design and operation of the needle recapping device as it relates to the above mentioned medical devices is typified in a first embodiment comprising a medical device including a needle having a proximal end secured to the medical device and a distal end terminating in a needle tip, the recapping device comprising shield means for shielding the distal needle end tip, the shield means comprising:

a. a hollow sleeve adapted for encircling a portion of the needle, the distal end opening of the hollow sleeve having means for enclosing an opening in the sleeve at the distal end, the enclosing means having an aperture therein which permits the distal needle end tip to slide therethrough, the sleeve being slidably movable along the needle between a first position on the needle, the first position being characterized by the distal tip of the needle projecting through the aperture at the distal end of the sleeve for a distance sufficient to enable use of the medical device and a second position on the needle being characterized by the distal needle end tip being enclosed within the sleeve and the enclosure means at the distal end of the hollow sleeve, and b. means for securing the sleeve to the medical device which permits free slidable movement of the hollow sleeve along the needle between the first and the second positions.

A further embodiment of the invention comprises a medical device comprising a hypodermic syringe having a hollow barrel having first and second opposite ends, a plunger slidably movable within the barrel and extending from the first barrel end, a hypodermic needle having a proximal end secured to and extending axially outward from the second opposite end of the barrel and a distal end terminating in a needle tip; the improvement comprising a needle recapping device which comprises shield means for shielding the distal needle end tip, the shield means comprising:

a. a hollow sleeve adapted for encircling a portion of the needle, the distal end opening of the hollow sleeve being capped, the cap having an aperture therein which permits the distal needle end tip to slide therethrough, the sleeve being slidably movable along the needle between a first position on said needle being characterized by the distal tip of the needle projecting from the distal end cap of the sleeve for a distance sufficient to enable use of the hypodermic syringe and a second position on the needle being characterized by the distal needle end top being contained within the distal end capped hollow sleeve, and b. means for securing the sleeve to the hypodermic syringe which permits free slidable movement of the hollow sleeve along the needle between the first and the second positions.

A further embodiment of the invention comprises a recapping device for use with a medical device adapted to penetrate human skin or the like, a distal end of the medical device terminating in a sharp tip, the recapping device comprising:

shield means for shielding the distal end sharp tip upon withdrawal of the sharp tip from a penetrated object, said shield means disposed on a portion of the medical device, a distal end of the shield means having an aperture therethrough permitting the shield means to be axially slidably movable along the medical device, the distal end aperture further adapted to permit the distal end sharp tip to slide therethrough, the shield means being adapted to slide on the medical device between a first position wherein the distal end sharp tip projects from the distal end of the shield means for a distance sufficient to enable use of the medical device and a second position on the medical device wherein the distal end sharp tip is contained within the distal end of the shield means; and means for securing the shield means to the medical device, the securing means permitting substantially free slidable movement of the shield means along the medical device between the first and the second positions.

DETAILED DESCRIPTION OF THE PREFERRED EMBODIMENTS

While the invention is satisfied by embodiments in many different forms, there are shown in the drawings, in which like reference numerals refer to like parts, and will herein be described in detail, preferred embodiments of the invention with the understanding that the present disclosure is to be considered as exemplary of the principles of the invention and is not intended to limit the invention to the embodiments illustrated. The scope of the invention will be measured by the appended claims and their equivalents.

Figure 1:
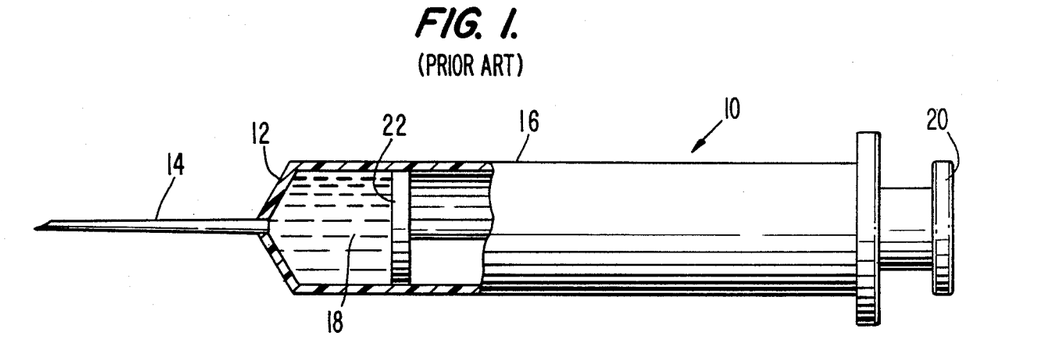
FIG. 1 is a side, elevational, partially sectional, view of a conventional hypodermic syringe.

FIG. 1 shows a conventional hypodermic syringe generally designated at numeral 10 including a shoulder portion 12 in which there is secured a permanent or disposable needle 14, and a barrel portion 16 having a chamber 18 for retaining fluid. A plunger assembly comprising push rod 20 and plate 22 for acting on fluid within chamber 18 is installed in barrel 16.

For purposes of the description of the present invention, when referring to the barrel portion 16 of the hypodermic syringe, the term "distal end" is intended to refer to the end furthest from the person holding the syringe, whereas the term "proximal end" is meant to refer to the end closest to the holder of the syringe. When referring to the needle 14, the term "distal end" is intended to refer to the point or tip 15 of the needle, i.e., the end furthest from the shoulder portion 12 and the term "proximal end" is intended to refer to the end installed in the shoulder portion 12.

Figure 2:
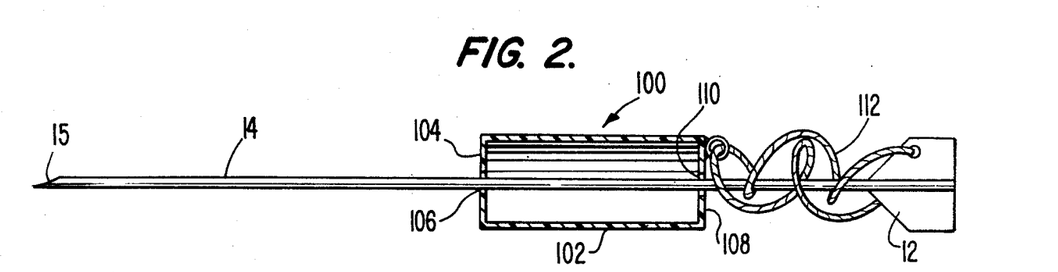
FIG. 2 is a side, elevational, partially sectional view of a preferred embodiment of the recapping device of the present invention.

FIG. 2 shows an embodiment of the recapping device of the invention generally designated 100 and surrounding needle 14 in a non-capped position. The device comprises a hollow sleeve or cylinder 102 capped at the end closest to the distal end of the needle 14 with an enclosure means or cap 104 which completely encloses or seals the open end of cylinder 102 except for aperture 106 which permits the cylinder 102 to slidably move along the shaft of needle 14. Optionally, the other end of the sleeve or cylinder 102 may also be similarly enclosed or capped with cap 108 having therein an aperture 110 which also permits facile, slidable movement of the cylinder along portion 12 of hypodermic syringe 10 with tether 112.

Use of the recapping device of the FIG. 2 embodiment of the invention is best illustrated in connection with use of a hypodermic syringe in a phlebotomy.

Figure 3A:
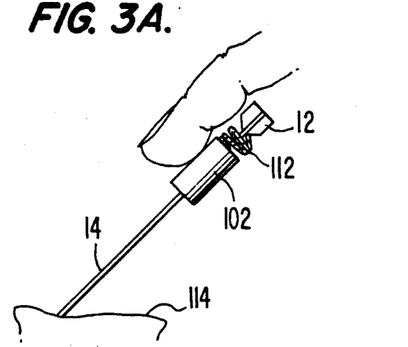
FIGS. 3a, b, c, are perspective views illustrating the recapping of a hypodermic syringe needle with the device of the present invention.

Referring to FIGS. 3a, b, c, the operation and basic principle of the recapping device is depicted. Hollow cylinder 102 initially surrounds the shaft of the needle 14 near the proximal end of the needle during storage and phlebotomy (the "first position"), and then slides over the needle point 15 (the "second position"), when the needle point 15 is lifted from the skin. Sliding of the cylinder 102 is driven by gravity in the usual phlebotomy position, as depicted, by inertia if the phlebotomist's hand is rapidly withdrawn or pushed away by sudden movement of the patient, or manually by simply pointing the needle tip down. Alternatively, the customary application of a cottonball to the phlebotomy site prior to needle withdrawal presents convenient means to manually draw the cylinder 102 to the "second position" as the needle point 15 leaves the skin, by holding the cotton ball against the cylinder. The cylinder is prevented from sliding completely off of the needle by tether 112, which is made to a length sufficient to permit cap 104 to extend past the needle point 15, but too short to permit the entire length of cylinder 102 terminating at cap 108 from extending past needle point 15. In an alternative design a stop (see, e.g. stop 48, FIGS. 6a, b) attached to approximately the midpoint of the needle shaft may be used to prevent cylinder 102 from sliding completely off of needle 14. The needle point 15, which is now enclosed within cylinder 102 and cap 104, is substantially prevented from finding its way out of the distal aperture 106 because the cylinder axis will not generally align with the needle axis after the needle is withdrawn from the aperture 106. The alignment of the cylinder axis is dependent on gravity, inertia, and the force exerted by the tether or stop, which are unlikely to maintain or return to perfect alignment with the needle axis for re-penetration of the aperture 106. This principle is extremely effective in achieving rapid protection of the point or tip with almost any type of needle motion after withdrawal, and in maintaining protection despite vigorous handling of the needle.

Figure 3B:
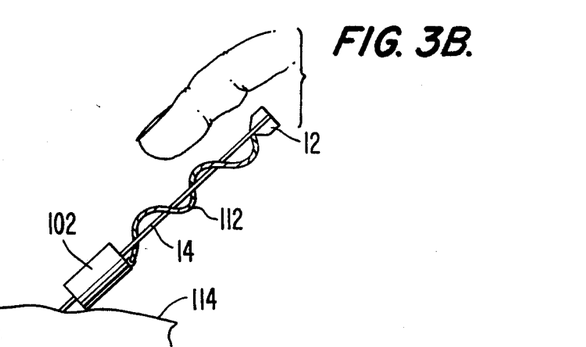
Figure 3C:
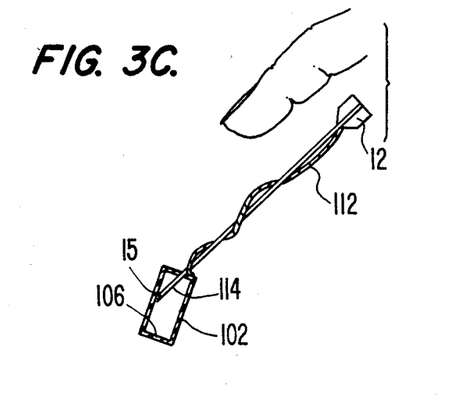

A complete operational cycle for a phlebotomy begins with removing a conventional plastic needle cover (not shown). The cylinder is held in the "first position" by the operator's finger until skin penetration is accomplished (FIG. 3a), and immediately released. The cylinder will travel to the skin 114, driven by gravity, because of the usual positioning of the needle 14 during phlebotomy (FIG. 3b). Although not completely necessary, directing the needle 14 downwardly at all times during the venipuncture will enhance quick protection of the needle tip 15 in the event of an inadvertent withdrawal. As soon as the tip of the needle is withdrawn from the skin, the downward orientation or direction of the needle causes the cylinder 102 to slide to the maximum extent of travel allowed by the tether 112. As soon as the needle tip 15 is completely enclosed inside the cylinder 102, the force of gravity along with any inertial moment applied to the cylinder by needle motion will cause the cylinder axis to change relative to the needle axis. Needle tip protection occurs at this "second position" (FIG. 3c). The needle will remain protected by the cylinder until it can be safely placed in a puncture-resistant plastic container, consistent with current practice.

The cylinder 102 portion of the device may be constructed of any of several puncture-resistent materials, such as metal, plastic, or ceramic. The tether 112 may be constructed of a strong flexible material such as silk, nylon, or mylar. Flexibility of the tether 112 must be sufficient to allow it to extend to full length under the expected forces that will drive the cylinder to the second position, including merely the force of gravity. For some applications, the tether may have elastic qualities that favor either the second positon, or the first position.

The embodiment depicted in FIG. 2, and shown in operation in FIG. 3 is especially preferred for applications involving entering an artery or vein, such as phlebotomy, as in such applications it is undesirable for a device to interfere with the user's feel of forces transmitted through the needle shaft. For instance, a phlebotomist feels a slight "pop" as the sharp needle enters a vein, signaling that the proper position has been reached. That position must be carefully maintained through the process of drawing blood. If the cylinder is held against the skin via a strong spring, the "feel" may be compromised. Similarly, if the cylinder were triggered to spring forward, there would be a jolt imparted to the needle system as that trigger released, a force imparted as the spring mechanism restored to its length, another jolt as the cylinder reached its destination, and perhaps another jolt as whatever locking mechanism activated to prevent the cylinder from sliding back to the unprotected-needle position.

The FIG. 2 embodiment of the present invention minimizes all of these disturbing forces. There is no spring, and only gravity and inertia operate on the cylinder. There is no force applied axially to the needle, because there is no spring and minimal resistance to cylinder sliding. There is no trigger, in that the user gently allows the cylinder to drop at the desired time. Finally, there is no locking mechanism, as the recapping device relies on the mechanical unlikelihood of realignment of the axis of the needle and the distal aperture 106, coupled with axial movement of the needle, before the needle tip would be exposed. A conventionally designed locking mechanism would generally require some degree of spring loading of the cylinder against the surface on which it slides, increasing friction, and decreasing feel.

For applications other than those requiring delicate touch, such as injection into blood specimen bottles, intravenous catheter ports, intramuscular and subcutaneous injection, some degree of spring-loading of cylinder travel and/or automatic triggering may be desirable. These can easily be realized in alternate embodiments of the present invention by adding elastic restoring force to the tether, and by providing various triggering devices that hold the cylinder from achieving the needle-protected position and release automatically after first penetration of a surface. It may be possible to employ these alternate embodiments for the more delicate operations such as phlebotomy although some amount of decreased feel would likely be evidenced.

FIGS. 4, 5, 6 and 7 depict alternative preferred embodiments of the recapping device of the present invention, all of which rely on a slidable hollow sleeve moving from a first position which enables the use of the needle, to a second position covering the tip of the needle upon withdrawal of the needle from the skin or from an intravenous catheter. These figures will be discussed below for the sake of providing a complete disclosure and for providing an understanding of ways in which the recapping device is envisioned for use with medical devices other than the hypodermic syringe.

Figure 4A:
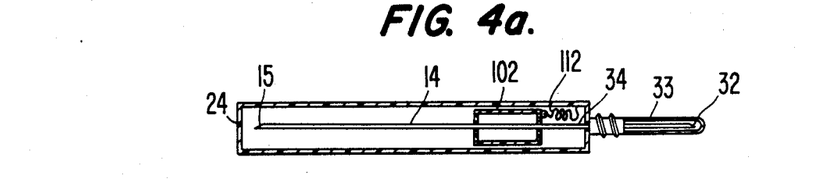
FIGS. 4a, b are side elevational, partially sectional views of a preferred embodiment of the recapping device of the present invention in use with a vacuum-tube phlebotomy set.
Figure 4B:
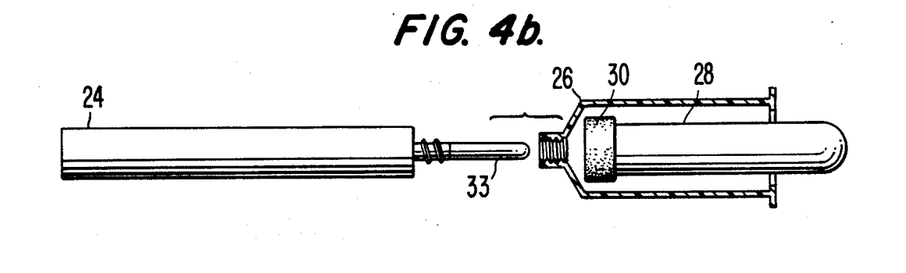

Referring first to FIGS. 4a and 4b, a vacuum tube phlebotomy set is depicted incorporating the recapping device of the present invention. A widely known brand of the vacuum tube set is known as the Vacutainer system, and such sets are commonly employed in lieu of the hypodermic syringe in phlebotomy applications, particularly where it is desired to take blood in more than one tube to perform more than one type of blood analysis with the blood removed from the patient.

FIG. 4a depicts a removable needle assembly employed in the Vacutainer system. Needle 14 is initially covered by protective cap 24 prior to use. Prior to removing protective cap 24, the needle assembly is threaded into hollow barrel 26, and the cap 24 is then removed. The hollow cylinder 102 and tether 112 are thus exposed at the proximal end of the needle 14. An evacuated tube 28, having a pierceable rubber top 30 is inserted into the hollow portion of barrel 26 to a point where the top 30 of the tube 28 is just touching needle extension 32, which is enshrouded by a flexible, resilent material 33.

The Vacutainer system is now configured to perform the phlebotomy in a manner similar to that shown in FIGS. 3a, b, c. The cylinder 102 is held in the "first position" until skin penetration is effected, as in FIG. 3a, and immediately released. The tube 28 is pushed forward in barrel 26, and is pierced by sharp needle extension 32, commencing the withdrawal of blood by the vacuum in the tube 28. Withdrawal of the tip of the needle from the skin is effected in a substantially identical manner as that depicted in FIG. 3c, and the recapping will therefore be effected by cylinder 102 described previously in this specification with respect to that figure.

The barrel 26 of the Vacutainer is reusable, thus the needle assembly is separated from the barrel after use. The tether 112 in this embodiment is therefore preferably attached to a needle hub 34 disposed at the proximal end of needle 14, and will be separated from the barrel together with the needle and hub.

Figure 5A:
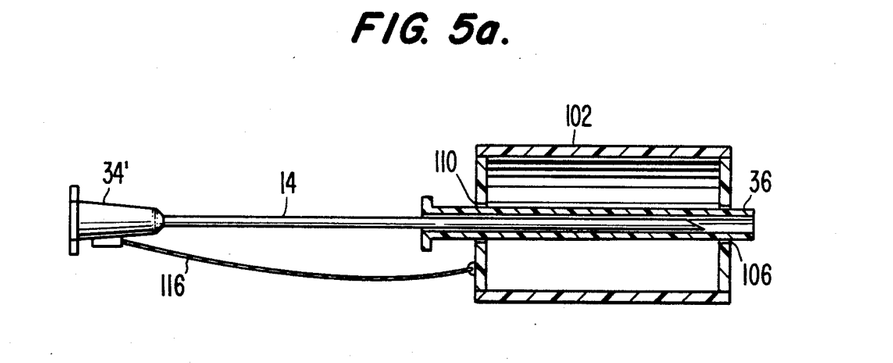
FIGS. 5a, b, c are side elevational, partially sectional views of an alternate preferred embodiment of the recapping device of the present invention.
Figure 5B:
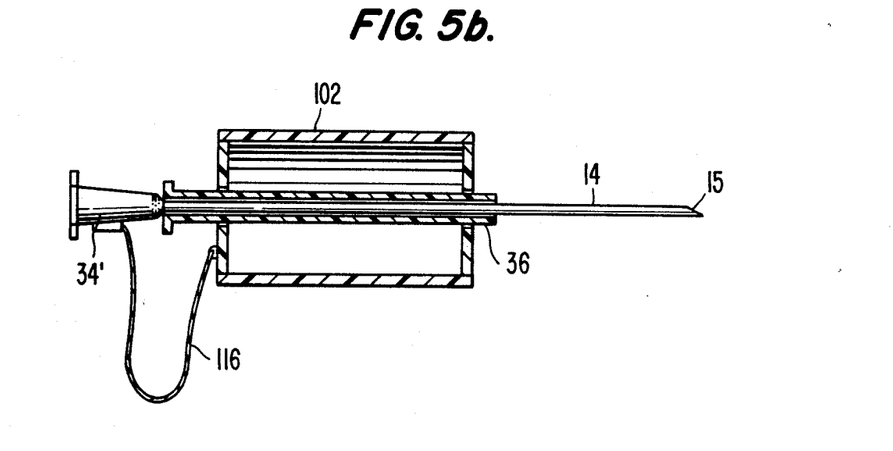
Figure 5C:
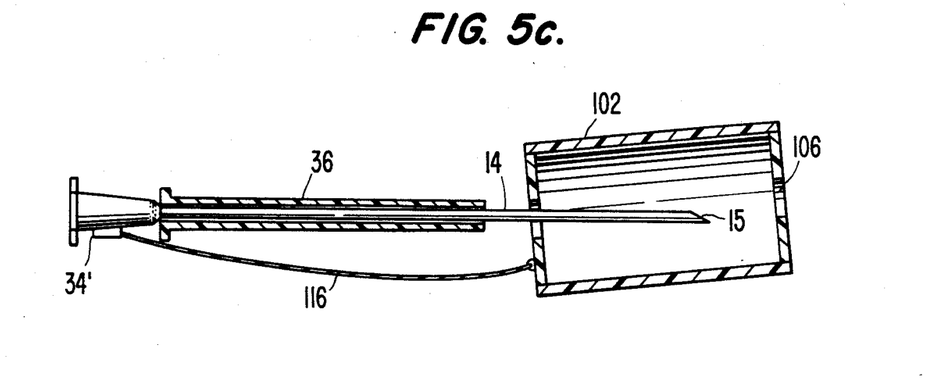

FIGS. 5a, b, c depict a modified version of the recapping device of the present invention. In these Figures, only the needle portion of the medical device is depicted, however, it is to be understood that such a needle will be readily adapted for use with hypodermic syringes, Vacutainer sets, and the like.

In this preferred embodiment, needle 14 is provided with a thin walled jacket 36 which surrounds needle 14 at the distal end thereof, covering tip 15 prior to use. Jacket 36 extends through apertures 106, 110 of cylinder 102, and serves to maintain axial alignment of the cylinder aperture axis with the needle axis. Attached to and extending between cylinder 102 and needle hub 34' is tether 116. In this particular embodiment, tether 116 possesses elastic properties biased in favor of its extended position (FIGS. 5a, 5c). The bias creates a restoring force on cylinder 102 favoring movement toward the second, distal end, position. An example of a suitable material for tether 116 is a thin nylon monofilament.

Operation of this preferred embodiment of the recapping device begins with the elements in the position depicted in FIG. 5a. As the tip 15 of needle 14 is brought into contact with, and penetrates through the skin 114 (FIG. 3a), jacket 36 and cylinder 102 slide back toward the proximal end or "first position" on needle 14, with very little resistance. The elastic or spring-like bias of tether 116 provides slight resistance to such movement, however, with the proper choice of materials, this resistance may be kept low enough such that this embodiment of the recapping device may be used even for the delicate venipuncture and arterial puncture applications wherein it is desirable to have forces transmitted through the needle shaft, to provide "feel", as described previously.

FIG. 5b depicts the needle and recapping device in a position analogous to that of FIG. 3b, wherein the needle tip 15 is disposed under the surface of the skin, and the distal end of cylinder 102 and jacket 36 rest at the surface of the skin. Upon removal of the needle tip 15 from the skin (see, e.g., FIG. 3c) the biased tether 116 urges aperture 106 of cylinder 102, independently of jacket 36, outwardly past the needle tip 15, thereby immediately effecting the enclosing and recapping of the needle 14. No longer is jacket 36 present at the distal end of the needle 14 to maintain axial alignment of needle 14 and cylinder 102.

This embodiment of the recapping device may be especially advantageously used where a venipuncture or arterial puncture is required with the needle orientation being other than downwardly pointing, as the slight spring force of tether 116 does not require the assistance of gravity in order to advance cylinder 102 to the second position covering the tip of needle 14.

Figure 6A:
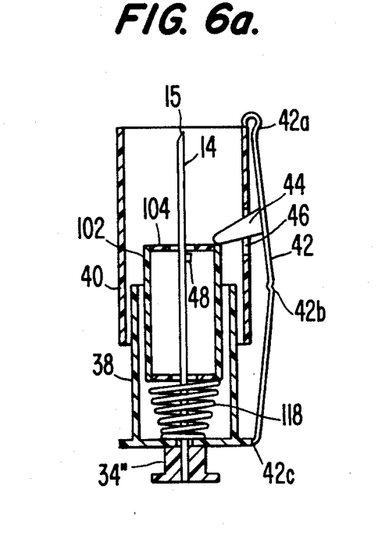
FIGS. 6a, b, are side elevational, partially sectional views of an alternate preferred embodiment of the recapping device of the present invention.
Figure 6B:
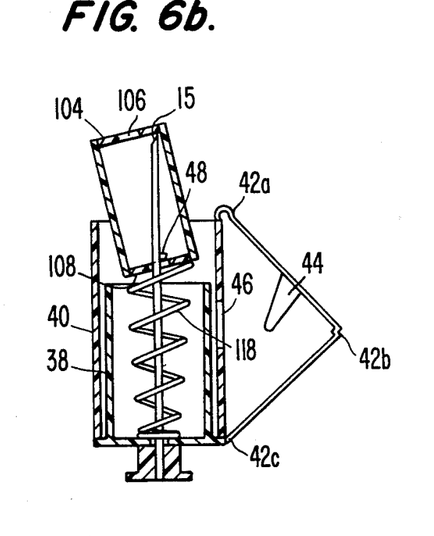

FIGS. 6a, b depict a further preferred embodiment of the recapping device of the present invention, which is primarily intended for use in applications where the delicate "feel" is not essential. Examples of such an application would be administering medications into an intravenous (IV) catheter port, penetration of vacuum tubes to deposit blood specimens, or for subcutaneous injections. The FIG. 6 embodiment possesses a stronger spring action which sacrifices some of the transmission of force or "feel", but provides improved recapping capabilities where, for example, the needle is pointed upwardly.

FIG. 6a shows the needle recapping device as configured prior to use. Needle 14 in this embodiment may preferably be shorter than, for example, a needle used for phlebotomy, in order to prevent pierce-through accidents with IV ports. Cylinder 102 is disposed at the first position near the proximal end of the needle. Recapping cylinder 102 in this embodiment is surrounded by telescoping intermediate and outer protective cylinders 38, 40, respectively. Intermediate cylinder 38 is fixedly connected to needle hub 34", and outer cylinder 40 is held in its extended initial position near the distal end of the needle 14 by a deformable arm 42, preferably attached to a proximal end of intermediate cylinder 38 and to a distal end of outer cylinder 40.

The proximal cap 108 of cylinder 102 is tethered to a cap of intermediate cylinder 38 disposed adjacent to needle hub 34", by coil spring 118. Coil spring 118 is in compression as depicted in FIG. 6a, and is positioned to urge cylinder 102 outwardly toward the distal end of the needle 14. Retaining tab 44 extends inwardly from arm 42 through an opening 46 in outer cylinder 40, and is configured to rest on distal cap 104 of cylinder 102 to retain cylinder 102 in the "first position".

In operation, needle tip 15 is used to penetrate the desired surface, contact with the surface thereby moving outer cylinder 40 axially toward needle hub 34" or the proximal end of the of the needle 14. As outer cylinder 40 travels toward the proximal end of the needle, arm 42 is configured to deflect outwardly, and is preferably provided with three joints 42a, 42b, and 42c, which are designed to be inelastically deformable. As the arm 42 deflects outwardly, retaining tab 44 is removed from engagement with distal cap 104 of cylinder 102, allowing spring 118 to act upon cylinder 102 urging the cylinder toward the distal end of the needle and into contact with the penetrated surface.

When needle tip 15 is removed from the penetrated surface, spring 118 will push distal cap 104 axially past needle tip 15, thus recapping the needle 14. Cylinder 102 is prevented from sliding completely off needle 14 in this configuration by a stop 48 protruding radially outwardly from the surface of the needle, which prevents proximal cap 108 from moving axially outwardly past the stop 48. A stop such as the one depicted in FIGS. 6a, b, previously mentioned as an alternative means to the tether 112 shown in FIGS. 3a, b, c, for preventing cylinder 102 from sliding completely off needle 14. As can be seen in FIG. 6b, as well as in FIG. 5c, because the spring 118 or tether 116 is preferably attached at an off-center-axis to cylinder 102, the spring or tether will assist in maintaining the misalignment of the distal aperture 106 of cylinder 102 with needle 14 by "cocking" the cylinder to one side.

Figure 7:
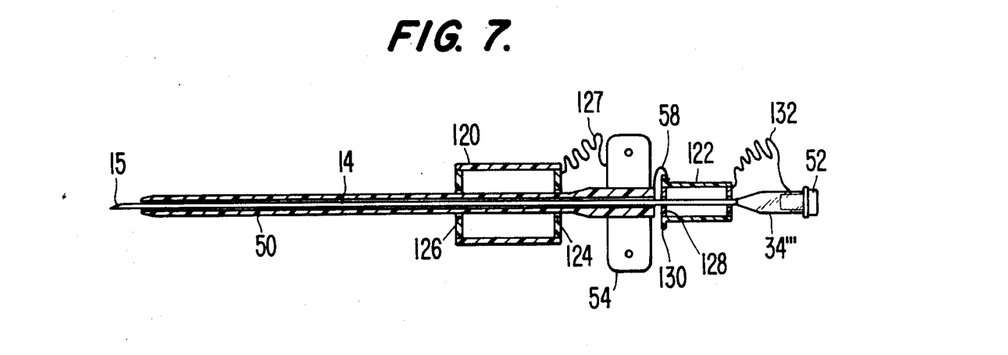
FIG. 7 is a side elevation, partially sectional view of an alternate preferred embodiment of the recapping device of the present invention in use with a catheter-over-needle system.

FIG. 7 depicts an embodiment of the recapping device of the present invention in use with a catheter-over-needle system. Currently, such systems are the most frequently used intravenous catheter in adult medicine. In this system, needle 14 is encased over a substantial portion of its length by flexible catheter 50. Needle 14 has, at its proximal end, a clear (transparent) or translucent hub 34''', which is adapted to receive a small volume of blood. Plug 52 is disposed at the end of hub 34''', and when the system is to be inserted into a vein, the plug may be removed and replaced with a hypodermic syringe (FIG. 1), as appropriate.

Needle 14 in this catheter-over-needle system is used to puncture the skin and vein, and, as desired, will transmit the previously discussed "feel" of proper insertion to the user. Further, hub 34''' will provide a visual indication of proper insertion of the needle and catheter by evidencing a "flashback" of blood through the needle which is visible through the hub. Generally, an unsuccessful attempt at insertion will result in the entire system as a unit being withdrawn from the patient. After a successful insertion, only the needle will be removed, leaving the catheter in the body extending between the vein and the surface of the skin.

The conventional catheter-over-needle system as modified in accordance with the present invention will preferably have two recapping cylinders 120, 122, in order to accommodate the two different modes of withdrawal from the patient. Cylinder 120 is slidingly disposed around the exterior surface of catheter 50, the proximal and distal apertures 124, 126, respectively, being of slightly larger diameter than the catheter 50. Cylinder 120 is connected to catheter hub 54 by tether 127. In the event that an insertion of the system is unsuccessful in penetrating the vein, the entire system (catheter and needle) is withdrawn, and cylinder 120 is used in a similar manner to that shown and described with respect to FIGS. 3a, b, c, wherein the user releases the cylinder 120 which drops under the force of gravity into contact with the skin. Upon complete withdrawal, cylinder 120 caps the end of the catheter 50 as well as needle tip 15.

A successful insertion of the needle and catheter into a vein will result in the withdrawal of the needle 14 from the interior of the catheter 50, and intravenous tubing will be connected in its place. In this mode of operation, cylinder 122 will be employed to recap the end of needle 14. A preferred way to accomplish this recapping is to provide the distal cap 128 of cylinder 122 with an outwardly extending flange 130, and to provide catheter hub 54 with a corresponding catch 58, adapted to engage flange 130, such that cylinder 122 is held near catheter hub 54 when needle 14 is being withdrawn. The net effect of the operation of the flange and catch is that cylinder 122 will slide axially along needle 14 to the distal end thereof during needle withdrawal. Upon full withdrawal, the needle tip 15 is capped by cylinder 122, which is pulled into place by catch 58. Cylinder 122 is prevented from completely sliding off needle 14 by tether 132 connected between cylinder 122 and needle hub 34'''.

The FIG. 7 embodiment employing the two recapping cylinders may advantageously be used in various other "needle-within-needle" arrangements. These include, for example, lumbar puncture needles, transthoracic pacemaker needles, small-bore chest tube/trocar devices, central venous access needles, and arterial access devices.

FIGS. 8-11 depict further alternative preferred embodiments of the present invention, wherein additional protection is provided against needle tip exposure, in a somewhat different manner, subsequent to the use and recapping of needle.

Figure 8A:
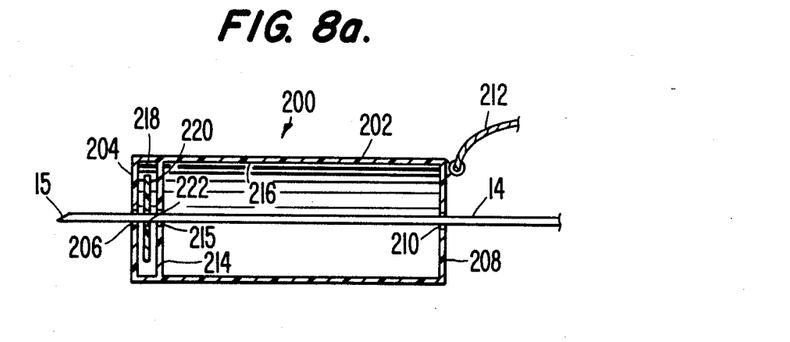
FIGS. 8a, b are cross-section and cutaway perspective views, respectively, of an alternate preferred embodiment of the present invention prior to use of the medical device.

FIGS. 8a, b provide cross-sectional and cutaway perspective views of a first of these alternative preferred embodiments prior to the occurrence of withdrawal of the needle 14 and recapping of the needle tip 15. Although only the needle 14 portion of the medical device is shown in these and the ensuing figures, it will be readily apparent that the depicted needle may be attached to any of the systems previously depicted in FIGS. 1-7. Further, it should be readily apparent that cylinder 202 depicted in FIGS. 8a, b and 9a, b, and cylinder 302 depicted in FIGS. 10a, b and 11a, b may be tethered or otherwise restrained on the medical device as shown in any of FIGS. 1-7.

Figure 8B:
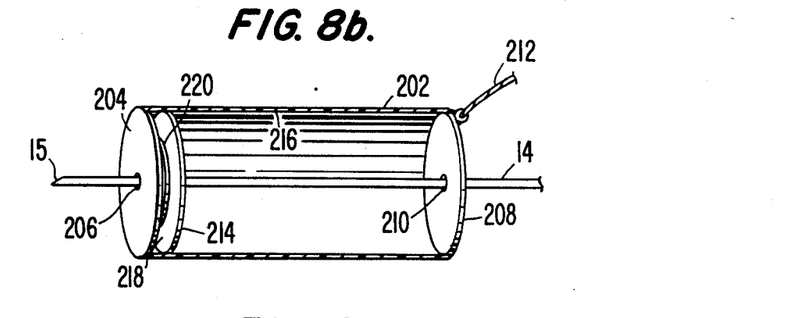

The recapping device 200 depicted in FIG. 8a, b, is shown surrounding needle 14 in a non-capped position. The device preferably comprises a substantially hollow sleeve or cylinder 202, capped at a distal end closest to the distal end of the needle with cap 204, which completely encloses or seals the open end of cylinder 202 except for aperture 206 which permits cylinder 202 to slidably move along the shaft of needle 14. Optionally, the proximal end of cylinder 202 may also be enclosed by cap 208 having therein an aperture 210 which permits facile, slidable movement of the cylinder along the needle. Tether 212 secures the recapping device 200 to a portion of a medical device (not shown) which is attached at the proximal end of needle 14. As described to this point, cylinder 202 of this embodiment is substantially identical to cylinder 102 depicted in FIG. 2.

Cylinder 202, however, further includes disc-shaped barrier means 214 disposed within cylinder 202, and which is preferably aligned parallel to and spaced apart from cap 204 at a predetermined distance axially inwardly of cap 204. The barrier is also preferably an integral element of cylinder 202 or is fixedly attached in position to an interior wall 216 of cylinder 202. Barrier 214 is designed to have aperture 215 disposed in axial alignment with aperture 206 of cap 204, thereby permitting axial movement of the cylinder with respect to the needle.

Distal cap 204 and barrier 214 form a hollow cylindrical housing 218 for axially retaining a fenestrated disk 220 having a central aperture 222 extending therethrough. Fenestrated disk 220 preferably has a peripheral diameter which is smaller than a diameter of interior wall 216.

Prior to use of the needle 14 in penetrating the skin or other surface, cylinder 202 is disposed on the needle 14 with tip or point 15 of needle 14 protruding through aperture 206 in cap 204. In order to protrude in this manner, the fenestrated disk aperture 222 must be in axial alignment with cap aperture 206 and barrier aperture 215, which, as previously indicated is fixed in axial alignment with cap aperture 206.

Figure 9A:
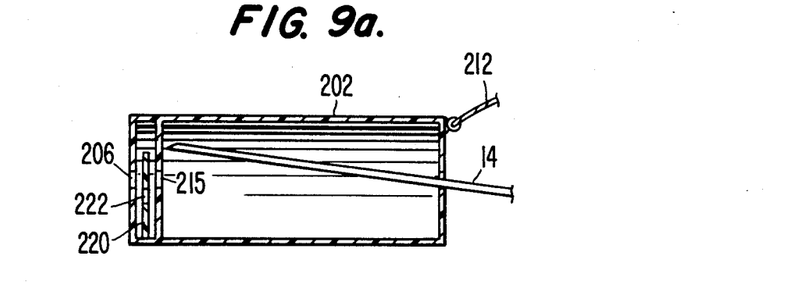
FIGS. 9a, b are cross-section and cutaway perspective views, respectively, of the FIG. 8 embodiment, after the medical device has been used.
Figure 9B:
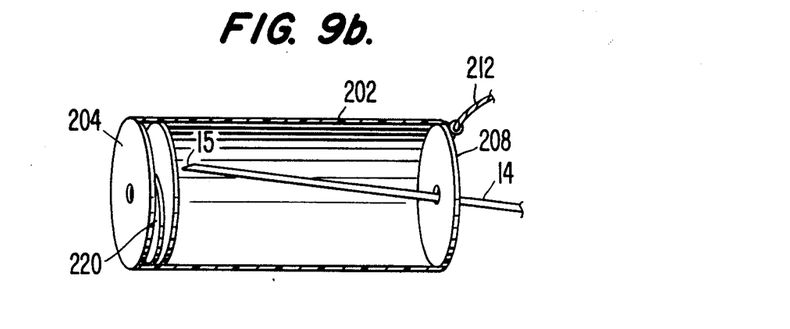

The axial movement of cylinder 202 to effect the self-recapping of the needle tip 15 will preferably be substantially identical to that shown in the sequence illustrated in FIGS. 3a-c, although the device 200 depicted in FIGS. 8 and 9 is well suited for use with any of the devices shown in FIGS. 1-7 herein. The cylinder 202 will travel from a first position wherein the tip 15 and the distal end of needle 14 protrude through the end cap 204, wherein the needle 14 may be employed to penetrate the skin or anohter surface, to a second position, depicted in FIGS. 9a, b wherein needle tip 15 self-retracts through cap aperture 206, fenestrated disk aperture 222 and barrier aperture 215 as cylinder moves axially outwardly with respect to the needle 14.

As depicted in FIGS. 9a, b, the needle tip is enclosed or captured within cylinder 202 when the cylinder has moved to its second position. The fenestrated disk 220 becomes substantially free floating within housing 218 once needle 14 has retracted through aperture 222, due to its smaller size. Thus, disk 220 will be displaced, and aperture 222 will move out of alignment with apertures 206 and 215, and the solid portion of the disk will obstruct the axial outward passage of needle tip 15 to distal cap aperture 204, thus substantially preventing needle tip 15 from repenetrating or protruding through cylinder 202. Repenetration of the distal cap aperture 206 would require the unlikely event of realignment of the axis of the needle, with the axis of the cylinder (i.e., apertures 206 and 215), as well as with the fenstration or aperture 222 of fenestrated disk 220. The cylinder 202 containing fenestrated disk 220 depicted in FIGS. 8 and 9 thus provides protection against repenetration in the form of both cylinder tilt with respect to the needle axis featured in the device embodied in FIGS. 1-7, combined with the freely moving fenestrated disk providing an obstruction between the fixedly aligned apertures 206, 215.

Figure 10A:
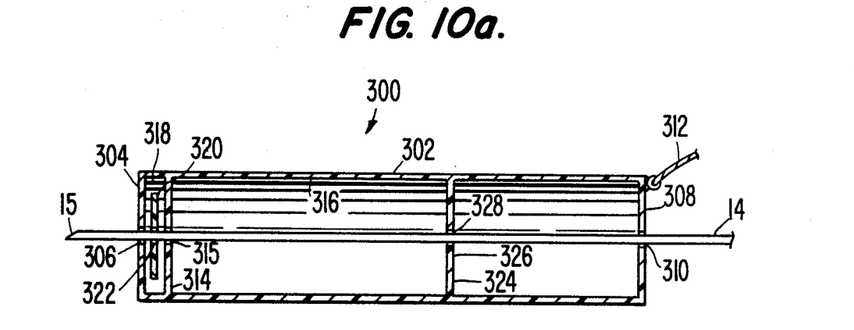
FIGS. 10a, b are cross-section and cutaway perspective views, respectively, of an alternate preferred embodiment of the present invention prior to use of the medical device.

The self-recapping device of the present invention will also protect against repenetration without the cylinder tilt previously discussed. FIGS. 10a, b, and FIGS. 11a, b depict an embodiment wherein a free-floating fenestrated disk provides the primary form of protection against repenetration, as the axis of the needle is permitted, by design, to remain in alignment with the distal aperture of device 300.

FIGS. 10a, b, show the recapping device 300 surrounding the needle 14 in a non-capped position. The device 300 preferably comprises hollow sleeve or cylinder 302, distal end cap 304 having distal aperture 306 extending therethrough, proximal end cap 308, proximal end cap aperture 310, tether 312, barrier 314 with aperture 315, the barrier 314 and distal end cap 304 forming housing 318, and fenestrated disk 320 having central aperture 322 therein, all elements being substantially identical to those described with respect to the embodiment shown in FIGS. 8 and 9.

Figure 10B:
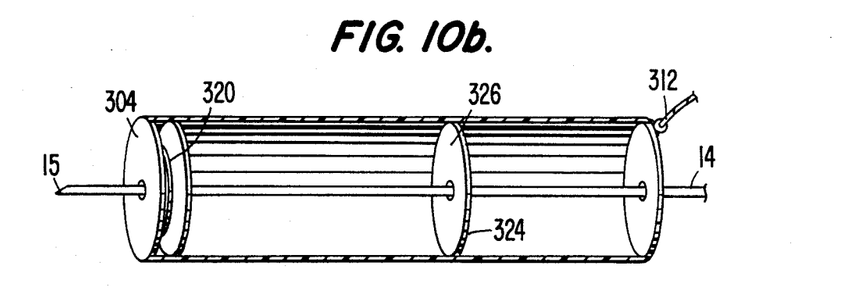
Figure 11A:
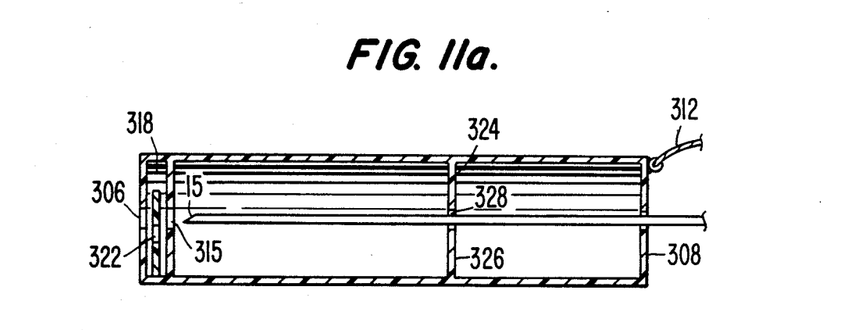
FIGS. 11a, b are cross-section and cutaway perspective views, respectively, of the FIG. 10 embodiment, after the medical device has been used.
Figure 11B:
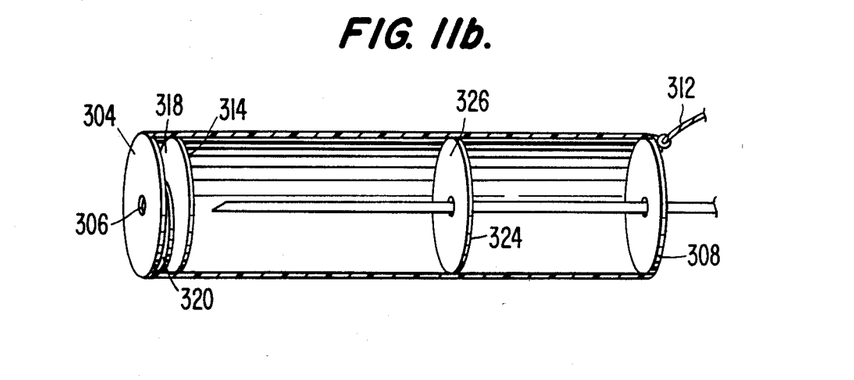

Cylinder 302 further contains an intermediate needle aligning means 324 disposed in an interior thereof in the form of intermediate aperture disk 326 as depicted in the preferred embodiment of FIGS. 10 and 11. Intermediate disk 326 has an aperture 328 extending therethrough in axial alignment with cap apertures 306, 310 as well as barrier aperture 315, and initially (FIGS. 10a, b) with fenestrated disk aperture 322.

The axial movement of device 300 between the first non-capped position and a second capped position takes place in a manner substantially identical to that described with respect to FIGS. 8 and 9. As needle tip 15 is retracted into cylinder 302, fenestrated disk 320 is freed to move within housing 318, and the fenestration or aperture 322 will move out of alignment (FIG. 11a) with the apertures 306, 315 of the distal end cap 204 and barrier 314. The intermediate apertured disk 326, coacting with proximal end cap 308, serves to retain the needle 14 and the cylinder 302 in substantial axial alignment.

The device 300 relies substantially entirely on the unlikelihood that the aperture 322 of the fenestrated disk 320 will become realigned with apertures 306, 315, coinciding with a forward movement of the needle 14 within the cylinder for protection against repenetration of the needle tip. Thus, this embodiment demonstrates that the recapping device of the present invention does not necessarily require a tilting of the cylinder axis with respect to the needle axis, although this tilting may provide enhanced protection against repenetration of the needle tip.

Variations in structure from the embodiments depicted in FIGS. 8-11 are also envisioned, for example, to facilitate manufacture of the recapping device. The intermediate needle aligning means 324, for example, may comprise a small ring having an aperture therethrough retained in proper axial alignment by one or more spoke-like members extending inwardly from the interior wall 316 of cylinder 302. In addition, an apertured ring suspended by spokes could be substituted for the proximal end cap in any of the embodiments depicted in the application, and could possibly be substituted for either the distal end cap (204, 304) or the barrier disc (214, 314), but probably not for both simultaneously. Further, it is not an absolute requirement that barrier 214 or 314 be of a disk configuration having a well-defined central aperture, but need only be of a design wherein it will securely retain (in an axial sense) the fenestrated disk in the housing formed by the barrier and the cylinder end cap, and wherein in it will not obstruct the axial passsage of the needle through the aperture in the end cap in the pre-use position.

One further variation from the embodiment depicted in FIGS. 8-11 which is envisioned would provide more than one fenestrated disk in the housing disposed in the cylinder. A plurality of the fenestrated disks of different diameters could be disposed in the housing making it even more unlikely that the needle tip will ever repenetrate the distal end of the recapping device, as all fenestrated disks would have to move into alignment in order for this to occur.

The foregoing description includes various details and particular structures according to preferred embodiments of the invention, however, it is to be understood that these are for illustrative purposes only. Various modifications and adaptations may become apparent to those skilled in the art. Accordingly, the scope of the present invention is to be determined by reference to the appended claims.

I claim:

1. A recapping device for use with a medical device including a needle or needle-like device having a proximal end secured to said medical device and a distal end terminating in a needle tip, said recapping device comprising shield means for shielding said distal needle end tip, said shield means comprising:
    a. a hollow sleeve adapted to encircle a portion of said needle, a distal end opening of said hollow sleeve having means for enclosing said opening in said hollow sleeve at said distal end, said enclosing means having an aperture therein adapted to permit the distal needle end tip to slide therethrough, said sleeve being freely slidably movable along said needle between a first position on said needle, said first position being characterized by said distal end tip of said needle projecting through said aperture at said distal end of said sleeve for a distance sufficient to enable use of said medical device and a second position on said needle being characterized by said distal needle end tip being enclosed within said sleeve and said enclosure means at said distal end of said hollow sleeve; and
    b. tether means for securing said sleeve to said medical device and for permitting substantially free slidable movement of said hollow sleeve along said needle from said first position to said second position, without said tether means exerting a biasing force on said sleeve toward either said first position or toward said second position.

2. The recapping device of claim 1 wherein said tether is secured to the proximal end of said sleeve.

3. The recapping device of claim 1 wherein said hollow sleeve is cylindrical.

4. The recapping device of claim 1 wherein a proximal end opening of said hollow sleeve has means for enclosing said sleeve, said proximal end enclosing means having an aperture therein which permits slidable movement therethrough of said medical device.

5. The recapping device of claim 1 wherein said enclosing means at said distal end of said sleeve comprises a cap oriented substantially perpendicularly to an axial direction of said sleeve, said cap having a central aperture therein.

6. The recapping device of claim 5 wherein said enclosing means further comprises a fenestrated element having an aperture therein, said fenestrated element being substantially flat in shape, said fenestrated element further being smaller than an interior cross-section dimension of said sleeve, and means for retaining said fenestrated element in an approximately parallel orientation to said distal end cap and for restraining said fenestrated element from moving in an axial direction.

7. The recapping device of claim 6 wherein a proximal end opening of said hollow sleeve has means for enclosing said end opening of said sleeve, said proximal end enclosing means having an aperture therein which permits slidable movement therethrough of said medical device.

8. The recapping device of claim 7 wherein said sleeve further comprises an intermediate needle aligning means disposed in an interior of said sleeve between said distal end and said proximal end, said intermediate needle aligning means having an aperture therein, said 9. A medical needle recapping device comprising:
   a. a hollow sleeve adapted to encircle a portion of said needle, a distal end opening of said hollow sleeve being capped, said cap having an aperture therein adapted to permit a distal needle end tip to slide therethrough, said sleeve being freely slidably movable along said needle between a first position on said needle being characterized by said distal end tip of said needle projecting from said distal end cap of said sleeve for a distance sufficient to enable use of said needle and a second position on said needle being characterized by said distal needle end tip being contained within said distal end capped hollow sleeve; and
   b. tether means for retaining said sleeve on said needle and for permitting substantially free slidable movement of said hollow sleeve along said needle from said first position to said second position, without said tether means exerting a biasing force on said sleeve toward either said first position or said second position.

10. The recapping device of claim 9 wherein said tether is secured to a proximal end of said sleeve.

11. The recapping device of claim 9 wherein said hollow sleeve is cylindrical.

12. The recapping device of claim 9 wherein a proximal end opening of said hollow sleeve is also capped, said proximal end cap having an aperture therein which permits slidable movement therethrough of said needle.

13. A recapping device for use with a medical device adapted to penetrate human skin or the like, a distal end of said medical device terminating in a sharp tip, the recapping device comprising:
   shield means for shielding said distal end sharp tip upon withdrawal of said sharp tip from a penetrated object, a distal end of said shield means having an aperture therethrough permitting said shield means to be freely axially slidably movable on said medical device,
   said shield means being adapted to freely slide on said medical device between a first position wherein said distal end sharp tip projects from said distal end of said shield means for a distance sufficient to enable use of said medical device and a second position on said medical device wherein said distal end sharp tip is enclosed within said shield means; and
   tether means for securing said shield means to said medical device and for permitting substantially free slidable movement of said shield means along said medical device from said first position to said second position, wherein said tether means exerts no biasing force on said shield means toward either said first position, or said second position.

14. The recapping device of claim 13 wherein said shield means comprises a first hollow sleeve having a cap at a distal end thereof, said aperture at said distal end being located on said cap.

15. The recapping device of claim 14 wherein said medical device comprises a needle, and said first hollow sleeve is disposed on said needle.

16. The recapping device of claim 15 wherein said medical device comprises a hypodermic syringe including said needle.

17. The recapping device of claim 15 wherein said medical device comprises a vacuum tube phlebotomy set including said needle.

18. The recapping device of claim 15 wherein said medical device further comprises a catheter surrounding an outer surface of said needle and extending axially from said distal end cap of said first hollow sleeve to a predetermined point adjacent to a tip of said needle.

19. The recapping device of claim 18 further comprising a second hollow sleeve having a cap at a distal end thereof, said second hollow sleeve disposed on a portion of said catheter, said distal end cap of said second hollow sleeve having an aperture therethrough permitting said second hollow sleeve to be axially slidably movable on said catheter, said second hollow sleeve being adapted to slide on said catheter between a first position wherein said needle tip and a distal end of said catheter project from said distal end of said second hollow sleeve for a distance sufficient to enable use of said medical device and a second position on said medical device wherein said needle tip and said distal end of said catheter are enclosed within said distal end of said second hollow sleeve; and
   means for securing said second hollow sleeve to said catheter, said securing means permitting substantially free slidable movement of said second hollow sleeve along said catheter between said first and said second positions.

20. The recapping device of claim 19 wherein said means for securing said first hollow sleeve is a first tether connected to said first hollow sleeve and to a hub of said needle.

21. The recapping device of claim 20 wherein said means for securing said second hollow sleeve is a second tether connected to said second hollow sleeve and to a hub of said catheter.

22. The recapping device of claim 14 wherein said hollow sleeve further comprises means for obstructing said distal end aperture when said hollow sleeve is moved to said second position.

23. The recapping device of claim 22 wherein said obstructing means comprises at least one free-floating disk having an aperture therein, said at least one disk being disposed in an interior of said hollow sleeve adjacent to said distal end cap.

24. The recapping device of claim 23 wherein said obstructing means further comprises means for retaining said at least one disk in a nearly parallel orientation to said distal end cap when said hollow sleeve is moved to said second position.

25. The recapping device of claim 24 wherein said retaining means further axially restrains movement of said at least one disk.

26. The recapping device of claim 25 wherein said retaining means comprises a barrier disk disposed in said hollow sleeve, said distal end cap and said barrier disk forming a housing within which said at least one disk is retained, said barrier disk having an aperture therein in axial alignment with said distal end aperture.

27. The recapping device of claim 22 wherein said hollow sleeve further comprises means for maintaining said hollow sleeve in axial alignment with said medical device when said sleeve is moved to said second position.

28. The recapping device of claim 27 wherein said aligning means comprises an aligning element fixedly attached to the interior of said sleeve intermediate of said distal end and a proximal end of said sleeve, said aligning element having an aperture therein in axial alignment with said distal end aperture, said aligning element aperture permitting said medical device to slide freely therethrough.

29. The recapping device of claim 14 wherein said hollow sleeve has a cap at a proximal end thereof, said proximal end cap having an aperture therein in alignment with said distal end aperture.

* * * * *

UNITED STATES PATENT AND TRADEMARK OFFICE
CERTIFICATE OF CORRECTION

PATENT NO. : 4,955,866

DATED : September 11, 1990

INVENTOR(S) : George A. COREY

It is certified that error appears in the above-identified patent and that said Letters Patent is hereby corrected as shown below:

Column 15, line 7;

In Claim 8, after line 5 thereof, insert the following:

-- aperture being in axial alignment with said aperture in said proximal end enclosing means, and with said aperture in said distal end enclosing means. --

Signed and Sealed this

Twenty-fifth Day of February, 1992

*Attest:*

HARRY F. MANBECK, JR.

*Attesting Officer*     *Commissioner of Patents and Trademarks*